(12) United States Patent
Urihara et al.

(10) Patent No.: US 6,372,789 B1
(45) Date of Patent: Apr. 16, 2002

(54) BACTERIOCIDE COMPOSITIONS FOR AGRICULTURAL AND HORTICULTURAL USE

(75) Inventors: Ichirou Urihara, Sakura; Hiroyuki Tsuboi, Yachiyo, both of (JP)

(73) Assignees: Dainippon Ink and Chemicals, Inc.; Nihon Bayer Agrochem K.K., both of Tokyo (JP); Bayer Aktiengesellschaft (DE)

( * ) Notice: Subject to any disclaimer, the term of this patent is extended or adjusted under 35 U.S.C. 154(b) by 0 days.

(21) Appl. No.: 09/582,753

(22) PCT Filed: Nov. 1, 1999

(86) PCT No.: PCT/JP99/06070

§ 371 Date: Jun. 30, 2000

§ 102(e) Date: Jun. 30, 2000

(87) PCT Pub. No.: WO00/25587

PCT Pub. Date: May 11, 2000

(30) Foreign Application Priority Data

Nov. 2, 1998 (JP) ............................. 10-312406

(51) Int. Cl.$^7$ .................. A01N 37/30; A01N 37/18; A01N 37/52
(52) U.S. Cl. .................. 514/555; 514/554; 514/613; 514/635
(58) Field of Search ................. 514/613, 635, 514/554, 555

(56) References Cited

U.S. PATENT DOCUMENTS

| | | | |
|---|---|---|---|
| 4,675,134 A | 6/1987 | Miura et al. | 260/501.14 |
| 5,532,262 A | 7/1996 | Brandes et al. | 514/388 |
| 5,672,619 A | 9/1997 | Brandes et al. | 514/417 |
| 5,728,734 A | 3/1998 | Sato | 514/555 |
| 5,922,762 A | 7/1999 | Brandes et al. | 514/525 |
| 5,962,518 A | 10/1999 | Stenzel et al. | 514/491 |

FOREIGN PATENT DOCUMENTS

| | | |
|---|---|---|
| AU | 699963 | 12/1998 |
| CN | 1094221 | 11/1994 |
| CN | 1132591 | 10/1996 |
| EP | 0 626 135 A2 | 11/1994 |
| EP | 0 707 792 | 10/1995 |
| JP | 6-329505 | 11/1994 |
| JP | 8-113505 | 5/1996 |
| JP | 8-208406 | 8/1996 |
| JP | 8-225402 | 9/1996 |

Primary Examiner—Allen J. Robinson
(74) Attorney, Agent, or Firm—Armstrong, Westerman & Hattori, LLP

(57) ABSTRACT

The novel agricultural and horticultural fungicidal compositions containing as active ingredients a combination of A) 1,1'-iminiodi(octamethylene)diguanidine of the formula (I)

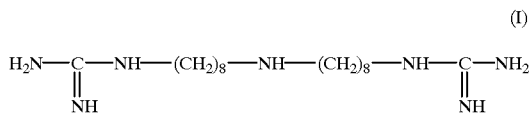

(iminoctadine) or an acid addition salt thereof and

B) 1,1'-iminiodi(octamethylene)diguanidine of the formula (II)

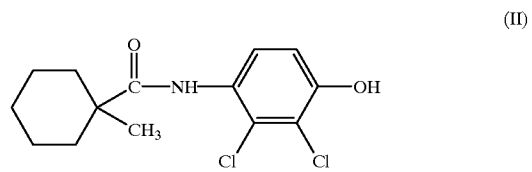

(fenhexamid)
are outstandingly active as fungicides.

4 Claims, No Drawings

BACTERIOCIDE COMPOSITIONS FOR AGRICULTURAL AND HORTICULTURAL USE

This application is a 371 of PCT/JP99/06070, filed Nov. 1, 1999.

TECHNICAL FIELD

The present invention relates to novel agricultural and horticultural compositions having fungicidal properties. The compositions contain the known iminoctadine and acid addition salts thereof on the one hand and the known N-(2,3-dichloro-4-hydroxy-phenyl)-1-methyl-cyclohexane carboxamide on the other hand.

BACKGROUND ART

It has already been known that iminoctadine and acid addition salts thereof are effective against a broad range of diseases that occur in important crop plants (see JP-A Sho 62-209003). Further, it has been described already that N-(2,3-dichloro-4-hydroxyphenyl)-1-methyl-cyclohexane carboxamide has a good fungicidal activity and is effective against gray mold in grapes and citrus fruits as well as against brown rot in peaches (see JP-A Hei 2-11551). However, the activity of these compounds is not always fully satisfactory for the control of severe infections with gray mold. Moreover, the control of gray mold fungus has become an even more serious problem due to the emergence of strains which are resistant to benzimidazoles, dicarboximides and diethofencarb

DISCLOSURE OF INVENTION

The present invention provides new compositions, which are excellently suitable for the control of phytopathogenic fungi, such as not only gray mold, but also fungal strains which are resistant to the above-mentioned agents. Furthermore, the compositions according to the invention are effective against a broad range of plant diseases even if the infection is severe.

The present invention has been completed after intensive research to resolve the above-mentioned problems. It has been found that compositions containing iminoctadine or acid addition salts thereof and N-(2,3-dichloro-4-hydroxyphenyl)-1-methyl-cyclohexane carboxamide are very effective against fungi causing disease in plants, including not only gray mold, but also strains, which are resistant to the above-mentioned agents. It has also been found that the compositions according to the invention exert an excellent control effect even if the infection is severe.

It has been found now that the novel agricultural and horticultural fungicidal compositions containing as active ingredients a combination of A) 1,1'-iminiodi(octamethylene)diguanidine of the formula (I)

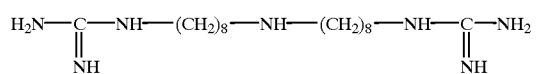

(iminoctadine) or an acid addition salt thereof and

B) N-(2,3-dichloro-4-hydroxy-phenyl)-1-methyl-cyclohexanecarboxamide of the formula (II)

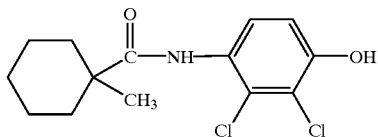

(fenhexamid)
exhibit a very good fungicidal activity.

Surprisingly, the fungicidal effect of the active compound combinations according to the invention is substantially greater than the sum of the effects of the individual active compounds. It is, therefore, a matter of an unforeseeable, genuine synergistic effect and not simply of an addition to the effect.

BEST MODE FOR CARRYING OUT THE INVENTION

The 1,1'-iminiodi(octamethylene)diguanidine is characterized by the formula (I) and is known under the common name iminoctadine.

Acid addition salts of iminoctadine include carboxylates, sulfonates, hydrochloride, carbonate, lauryl sulfate, sulfate, phosphate and the like. Examples of carboxylates include acetate, oxalate, laurylate, oleate, citrate and the like. Examples of sulfonates include alkyl sulfonate, alkyl benzene sulfonate, and the like. Examples of alkyl sulfonates include lauryl sulfonate, dodecyl sulfonate and the like.

Examples of alkyl benzene sulfonates include dodecyl benzene sulfonate, p-toluene sulfonate and the like. Preferred acid addition salts are carboxylates and sulfonates, such as alkyl benzene sulfonates. Particularly preferred are alkyl benzene sulfonates having 1 to 18 carbon atoms, specifically 10 to 13 carbon atoms, in the alkyl group.

The 1,1'-iminiodi(octamethylene)diguanidinium tris (alkyl-benzenesulfonate) [iminoctadine-tris(albesilate)] may be mentioned as an example of an acid addition salt of iminoctadine. This compound can be represented by the following formula (Ia)

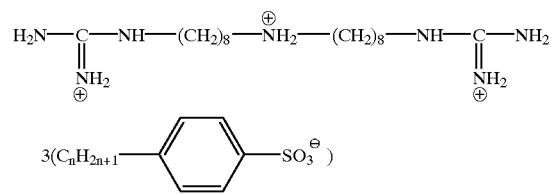

n=10 to 13.
[iminoctadine tris(albesilate)].

The iminoctadine of the formula (I) and acid addition salts thereof are known (see JP-A Sho 62-209003 and "The Pesticide Manual", 11th Edition 1997, pages 709–712).

The N-(2,3-dichloro-4-hydroxy-phenyl)-1-methyl-cyclohexane carboxamide of the formula (II) is also a known compound (see JP-A Hei 2-11551 and EP-A 0339418).

The synergistic effect is particularly clear when the active compounds are present in the compositions according to the invention in particular weight ratios. However, the weight ratios of the active compounds can be varied within a relatively wide range. In general, from 0.5 to 10 parts by weight, preferably from 1 to 5 parts by weight, of the compound of the formula (II) are allotted to 1 part by weight of a compound of group (A).

The agricultural and horticultural fungicidal compositions according to the invention possess very good fungicidal properties and can be used for the control of phytopathogenic fungi in agriculture and horticulture. They are suitable for the control of fungi, which are resistant to some other chemical compounds, and against fungi causing plant diseases, such as late blight, gray mold, leaf mold, leaf spot, anthracnose, and early blight in tomatoes; downy mildew, powdery mildew, gray mold anthracnose, gummy stem blight, phytophthora rot, scab, and Corynespora leaf spot in cucumbers; stem blight, leaf spot and gray mold in asparagus; anthracnose and gray mold in strawberries; powdery mildew, anthracnose, and gummy stem blight in pumpkins; Sclerotinia rot in cabbages; anthracnose in garland chrysanthemums; powdery mildew, Sclerotinia rot, anthracnose and gummy stem blight in watermelons; alternaria leaf spot, gray mold, and gray mold neck rot in onions; powdery mildew, gray mold and black rot in eggplants; alternaria leaf spot in welsh onions; leaf spot and alternaria leaf spot in Chinese cabbages; Sclerotinia rot and gray mold in peppers; powdery mildew, anthracnose, and gummy stem blight in melons; gray mold in lettuce; scab and gray mold in Japanese apricots; powdery mildew, anthracnose, gray mold and leaf spot in Japanese persimmons; gray mold and scab in citrus fruits; scab, black spot and physalospora canker in Japanese pears; gray mold, ripe rot, leaf spot, anthracnose, gummy stem blight, black rot, and swelling arm in grapes; scab, brown rot, Phomopsis rot, and anthracnose in peaches; scab, alternaria leaf spot/ring rot, blotch, sooty blotch, fly speck, fruit spot, and blossom blight in apples; stalk blight anthracnose, gray mold and Sclerotinia rot in Azuki beans; anthracnose, gray mold, and Sclerotinia rot in kidney beans; ring spot in broad beans; purple speck in soybeans; powdery mildew in tobacco; Romalaria leaf spot and cercospora leaf spot in sugar beets; anthracnose, gray blight, shoot blight and gray mold in tea; and black spot, anthracnose, gray mold, and powdery mildew in flowers. In particular, the agricultural and horticultural fungicidal compositions according to the invention are suitable for the control of fungi, which are resistant to some other chemical compounds, and against fungi causing plant diseases, such as gray mold in tomatoes, cucumbers, eggplants, and strawberries, or gray mold in fruits such as grapes, peaches, and citrus fruits.

The agricultural and horticultural fungicidal compositions can be used during the growing period of crops such as asparagus, strawberries, pumpkins, cabbages, cucumbers, garland chrysanthemums, watermelons, onions, tomatoes, eggplants, green onion, Chinese cabbages, peppers, spinach, Oriental melons, melons, lettuces, Japanese apricots, Japanese persimmons, citrus fruits, Japanese pears, grapes peaches, apples, Azuki beans, kidney beans, broad beans, soybeans, tobacco, sugar beets, tea, and flowers (i.e., roses, chrysanthemums, carnations, cyclamen, gentian, etc.). For grapes in particular, the agricultural and horticultural fungicidal composition can be preferably used between the stage prior to flowering and the young fruit stage in their growing period.

The agricultural and horticultural fungicidal compositions according to the invention can be used as such or in the form of customary formulations, such as wettable powders, suspension concentrates, dustable powders, emulsifiable concentrates, oil miscible liquids, tablets, granules, aerosols and the like. The formulations can be prepared by customary methods, for instance by mixing the active compounds with other components, such as extenders, surfactant agents, other additives, or suitable carriers, including water. The agricultural and horticultural fungicidal compositions according to the invention are preferably used in the form of wettable powders or suspension concentrates.

Examples of extenders include kaolins, clays, talc, chalk, quartz, attapulgite, montmorrillonite, diatomaceous earth, calcium carbonate, hydrated lime, quartz sand, ammonium sulfate, carbamide, vermiculite, wood chips, starch, clay, talc, bentonite, white carbon, etc., in the case of solid carriers, and alcohols, kerosene, naphtha, aromatic compounds (xylene, toluene, phenol, etc.), alkyl naphthalene, cyclohexane, benzene, acetone, N-methyl pyrrolidone and the like in the case of liquid carriers.

Examples of surfactant agents include polyoxysorbitan monooleate, ethylene oxide/propylene oxide copolymers, lignin sulfonate, sorbitan ester, soaps, alkyl benzene sulfonate, fatty acid amine salts, quaternary ammonium salts, alkyl pyridinium salts, alkyl aminoethyl glucine, alkyl dimethyl betaine, polyglycol sulfate ester, alkyl amino sulfonate, isopropyl phosphate, carboxymethyl cellulose, hydroxypropyl cellulose, xanthane gum, diaryl alkyl disulfonate, alcohol sulfate, alkyl aryl sulfonate, polyoxyethylene alkyl aryl ether, polyoxyethylene glycol ether, polyoxyethylene sorbitan monoalkylate, and the like.

Other additives include adjuvants like carboxymethyl cellulose, ethylene glycol and propylene glycol, as well as additives typically used during formulation.

The formulations generally contain between 30 and 90 per cent by weight of the active compounds, preferably between 50 and 80 per cent by weight. The active compounds can be present in the formulations in admixture with other known active compounds, such as fungicides, insecticides, acaricides, nematicides, fertilizers and plant-growth regulators.

The agricultural and horticultural fungicidal composition according to the invention are preferably used in the form of dispersions, which can be obtained by diluting the formulations with water. It is also possible to add other fungicides or pesticides to the formulations and then to disperse them. The concentration of the active compounds in the dispersions can be varied according to the period of use, method, site, form of the agent, targeted disease and targeted crop. However, the range for the acid addition salt of the iminoctadine is between 25 and 24,000 ppm, preferably between 60 and 200 ppm (when using iminoctadine, between 7.8 and 7,500 ppm, preferably between 19 and 63 ppm), while the range for fenhexamid is between 100 and 40,000 ppm, preferably between 150 and 300 ppm. In particular, in the case where the composition is used for fruits such as grapes and peaches, the concentration of the active compounds in the dispersions is such that the range for the acetic acid salt of the iminoctadine is between 25 ppm and 24,000 ppm, preferably between 200 ppm and 1,000 ppm (when using iminoctadine, between 7.8 ppm and 7,500 ppm, preferably between 62 ppm and 313 ppm), while the range for the fenhexamid is between 100 ppm and 40,000 ppm, preferably between 250 ppm and 1,500 ppm.

The dispersing amount will vary depending on the period of use, method, site, form of the agent, target disease, target crop, etc. For example, when spraying over vegetables such as tomatoes and cucumbers, the amount of the agent in the concentration of the effective component that is dispersed is preferably between 150 and 300 L per 10 are, while when spraying over fruits such as grapes and peaches, the amount of agent in the concentration of the effective component that is dispersed is preferably between 200 and 700 L per 10 are.

EXAMPLES

The present invention is illustrated by the following examples and use examples without being limited thereto. The term "part", as used below, means "parts by weight".

Example 1

(Wettable Powder 1)

| | |
|---|---|
| iminoctadine tris (albesilate) | 200 parts |
| fenhexamid | 300 parts |
| clay | 210 parts |
| lignin sodium sulfonate | 20 parts |
| polyoxyethylene alkyl phenyl ether | 50 parts |
| polyvinyl alcohol | 20 parts |
| white carbon | 200 parts |
| | 1000 parts |

The above-mentioned components are placed in a ribbon mixer, mixed well, and were pulverized sufficiently in an atomizer to obtain a wettable powder.

Example 2

(Wettable Powder 2)

| | |
|---|---|
| iminoctadine tris (albesilate) | 120 parts |
| fenhexamid | 200 parts |
| clay | 470 parts |
| lignin sodium sulfonate | 20 parts |
| polyoxyethylene alkyl phenyl ether | 50 parts |
| polyvinyl alcohol | 20 parts |
| white carbon | 120 parts |
| | 1000 parts |

The above-mentioned components are placed in a ribbon mixer, mixed well, and were pulverized sufficiently in an atomizer to obtain a wettable powder.

Example 3

(Wettable Powder 3)

| | |
|---|---|
| iminoctadine tris (albesilate) | 40 parts |
| fenhexamid | 400 parts |
| clay | 430 parts |
| lignin sodium sulfonate | 20 parts |
| polyoxyethylene alkyl phenyl ether | 50 parts |
| polyvinyl alcohol | 20 parts |
| white carbon | 40 parts |
| | 1000 parts |

The above-mentioned components are placed in a ribbon mixer, mixed well, and were pulverized sufficiently in an atomizer to obtain a wettable powder.

Example 4

(Wettable Powder 4)

| | |
|---|---|
| iminoctadine tris (albesilate) | 200 parts |
| fenhexamid | 100 parts |
| clay | 310 parts |
| lignin sodium sulfonate | 20 parts |
| polyoxyethylene alkyl phenyl ether | 50 parts |
| polyvinyl alcohol | 20 parts |
| white carbon | 300 parts |
| | 1000 parts |

The above-mentioned components are placed in a ribbon mixer, mixed well and were pulverized sufficiently in an atomizer to obtain a wettable powder.

Example 5

(Suspension Concentrate 1)

| | | |
|---|---|---|
| A) | iminoctadine tris (albesilate) | 120 parts |
| | polyoxyethylene lauryl ether | 30 parts |
| | sorbitan oleic acid ester | 30 parts |
| | propylene glycol | 50 parts |
| | water | 290 parts |
| | | 520 parts |
| B) | fenhexamid | 200 parts |
| | polyoxyethylene styryl phenyl ether | 30 parts |
| | water | 250 parts |
| | | 480 parts |

A) was mixed well in a homogenizer and dispersed, while B) was wet-ground in a bead mill. A) and B) were then thoroughly mixed together to form a suspension concentrate.

Comparative Agent 1 (Iminoctadine Tris(albesilate) Wettable Powder)

| | |
|---|---|
| iminoctadine tris (albesilate) | 400 parts |
| polyoxyethylene lauryl ether | 50 parts |
| clay | 150 parts |
| white carbon | 400 parts |
| | 1000 parts |

The above-mentioned components were placed in a ribbon mixer, mixed well, and were pulverized thoroughly with an atomizer to obtain a wettable powder.

Comparative Agent 2 (Fenhexamid Wettable Powder)

Fenhexamid wettable powder (effective component 50% by weight) manufactured by Japan Bayer Agrochem.

Comparative Agent 3

3-(3,5-dichlorophenyl)-N-isopropyl 2,4-dioximidazolidine-1-carboxamide (hereinafter referred to as IPRODIONE) wettable powder (effective component 50% by weight) manufactured by Nissan Chemical Industry Co.

Comparative Agent 4

N-(4-methyl-6-prop-1-ynylpyrimiidin-2-yl) aniline (hereinafter referred to as MEPANIPYRIM) wettable powder (effective component 40% by weight) manufactured by Kumiai Chemical Industry Co.

Use Examples

Example A

Test of Control Effect on Gray Mold in Cucumbers 18 cucumber plants (commercial name: ANKORU 8) cultivated under ordinary conditions at room temperature were assigned for each agent. Tangerines inoculated with gray mold fungi (resistant/sensitive strain: benzimidazole resistant, dicarboximide sensitive) provided by Japan Plant Protection Association were suspended to serve as inoculation sources. Each of the agents was diluted with water so that the active compounds reached the values shown in the table. Cucumbers at the 10-leaf stage at the start of the experiment were sprayed a total of 4 times at one week intervals using a compressed air sprayer to disperse a sufficient amount (300L/10a) of the diluted solutions of each of the agents. Prior to each spraying, the number of harvested fruit and the number of infected fruit were noted. One week after the last spraying, all fruit was assessed for the infected fruit, and a value was obtained for the occurrence rate of diseased fruit. Control values (%) were calculated using Equation 1 below. These results are shown in Table 1.

$$\text{Control value} = \frac{(\text{disease occurrence rate when untreated} - \text{disease occurrence rate with single or combined agent}) \times 100}{\text{disease occurrence rate when untreated}} \quad \text{Equation 1}$$

The additive effect obtained when two types of agents are mixed together can be expressed as the control value's expected value (%) (hereinafter, referred to as PE) indicated in Equation 2. Therefore, it is possible to determine the presence or absence of a "synergistic effect" from the relationship with the actual control value for the mixed agent.

$$\text{Control value's expected value} = (m+n) - \frac{mn}{100} \quad \text{Equation 2}$$

m and n in the above equation indicate the control values for iminoctadine tris(albesilate) and fenhexamid respectively.

The control value's expected values are shown inside parenthesis under the control value column in Table 1. Determination of the synergistic effect was made based on the following standards.

PC>PE: synergistic effect
PC=PE: additive effect
PC<PE: antagonistic effect.

TABLE 1

| Sample Agent | Effective component and its concentration (ppm) | | Disease occurrence rate (%) | Control value |
|---|---|---|---|---|
| wettable powder 1 | iminoctadine tris (albesilate) | 200 ppm | 1.3 | 94.6 |
|  | fenhexamid | 300 ppm |  | (84.5) |
| comparative agent 1 | iminoctadine tris (albesilate) | 200 ppm | 7.9 | 67.1 |
| comparative agent 2 | fenhexamid | 300 ppm | 11.3 | 52.9 |
| comparative agent 4 | MEPANIPYRIM | 200 ppm | 10.7 | 55.4 |
| untreated |  |  | 24.0 |  |

The control value for gray mold in cucumbers for wettable powder 1 was superior to comparative agent 1 and 2 which were used separately, and was also better than conventional comparative agent 4. The control value for gray mold in cucumbers for wettable powder 1 was higher than the control value's expected value obtained from the control values of comparative agents 1 and 2, thus confirming the synergistic effect of the agricultural and horticultural fungicidal composition according to the invention.

Example B

Test of Control Effect on Gray Mold in Tomatoes 18 tomato plants (commercial name: MOMOTARO) cultivated under ordinary conditions at room temperature were assigned to each agent. Tangerines inoculated with the same gray mold fungi as in Example A (R/S Strain) were suspended to serve as inoculation sources. Each of the agents was diluted with water so that the active compounds achieved the values shown in the table. Tomatoes at the 10 leaf stage at the start of the experiment were sprayed a total of 5 times at one week intervals using a shoulder-mounted compressed air sprayer to disperse a sufficient amount (476L/10a) of the diluted solutions of each of the agent. Prior to each spraying, the number of harvested fruit and the number of infected fruit was noted. One week after the last spraying, the total number of fruit was assessed for the infected fruit, and a value was obtained for disease occurrence rate. Control values were calculated using Equation 1 above. The results are shown in Table 2. The control value's expected values were determined using Equation 2, and are shown inside parenthesis under the control value column in Table 2.

TABLE 2

| Sample Agent | Effective component and its concentration (ppm) | | Disease occurrence rate (%) | Control value |
|---|---|---|---|---|
| wettable powder 2 | iminoctadine tris (albesilate) | 120 ppm | 1.5 | 93.7 |
|  | fenhexamid | 200 ppm |  | (84.5) |
| Suspension concentrate 1 | iminoctadine tris (albesilate) | 120 ppm | 1.1 | 95.5 |
|  | fenhexamid | 200 ppm |  | (84.5) |
| comparative agent 1 | iminoctadine tris (albesilate) | 120 ppm | 8.5 | 64.4 |
| comparative agent 2 | fenhexamid | 200 ppm | 10.4 | 56.5 |
| comparative agent 3 | IPRODIONE | 333 ppm | 14.4 | 39.7 |
| untreated |  |  | 23.9 |  |

The control values for gray mold in tomatoes for wettable powder 2 and suspension concentrate 1 were superior to that of comparative agents 1 and 2 which were used separately, and was also better than conventional comparative agent. The control value for gray mold in tomatoes for wettable powder 2 and suspension concentrate 1 was higher than the control value's expected value obtained from the control values of comparative agents 1 and 2, thus confirming the synergistic effect of the agricultural and horticultural fungicidal composition according to the invention.

Example C

Test of Control Effect on Gray Mold in Eggplants 9 eggplants (commercial name: SENRYO No. 2) cultivated under ordinary conditions at room temperature were assigned to each agent. Tangerines inoculated with the same gray mold fungi as in Example A (R/S stain) were suspended to serve as inoculation sources. Each of the agents was diluted with water so that the active compounds achieved the values shown in the table. Eggplants at the 8-leaf stage at the start of the experiment were sprayed of a total of 5 times at one week intervals using a compressed air sprayer to disperse a sufficient amount (300L/10a) of the diluted solutions of each of the agents. Prior to each spraying, the number of harvested fruit and the number of infected fruit was noted. One week after the last spraying, the total number of fruit was assessed for the infected fruit, and a value was obtained for disease occurrence rate. Control values were calculated using Equation 1 above. The results are shown in Table 3. The control value's expected values were determined using Equation 2, and are shown inside parenthesis under the control value column in Table 3.

TABLE 3

| Sample Agent | Effective component and its concentration (ppm) | | Disease occurrence rate (%) | Control value |
|---|---|---|---|---|
| wettable powder 1 | iminoctadine tris (albesilate) | 133 ppm | 12.5 | 80.5 |
| | fenhexamid | 200 ppm | | (67.3) |
| comparative agent 1 | iminoctadine tris (albesilate) | 133 ppm | 33.6 | 47.6 |
| comparative agent 2 | fenhexamid | 200 ppm | 40.0 | 37.6 |
| wettable powder 3 | iminoctadine tris (albesilate) | 27 ppm | 18.5 | 71.1 |
| | fenhexamid | 267 ppm | | (64.8) |
| comparative agent 1 | iminoctadine tris (albesilate) | 27 ppm | 44.8 | 30.1 |
| comparative agent 2 | fenhexamid | 267 ppm | 32.3 | 49.6 |
| wettable powder 4 | iminoctadine tris (albesilate) | 200 ppm | 16.8 | 73.8 |
| | fenhexamid | 100 ppm | | (68.1) |
| comparative agent 1 | iminoctadine tris (albesilate) | 200 ppm | 25.6 | 60.1 |
| comparative agent 2 | fenhexamid | 100 ppm | 51.2 | 20.1 |
| comparative agent 3 | IPRODIONE | 333 ppm | 35.0 | 45.4 |
| untreated | | | 64.1 | |

The effect of the comparative agent was not very high when the infection was severe. In contrast, the control value of wettable powders 1, 3, and 4 on gray mold in eggplants was superior to that of comparative agents 1–3. The control value of wettable powders 1, 3 and 4 on gray mold in eggplants was higher than the control value's expected value obtained from the control values of comparative agents 1 and 2, thus confirming the synergistic effect of the agricultural and horticultural fungicidal compositions according to the invention.

INDUSTRIAL APPLICABILITY

As explained above, agricultural and horticultural fungicidal compositions containing iminoctadine or acid addition salts thereof and fenhexamid are very effective in controlling phytopathogenic fungi, such as gray mold and fungal strains which are resistant to chemical compounds.

What is claimed is:
1. Agricultural and horticultural fungicidal compositions, comprising as active ingredients a synergistic fungicidally effective combination of
A) 1,1'-iminiodi(octamethylene)diguanidine of the formula

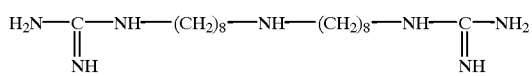

or an acid addition salt thereof and
B) N-(2,3dichloro-4-hydroxy-phenyl)-1-methyl-cyclohexane carboxamide of the formula

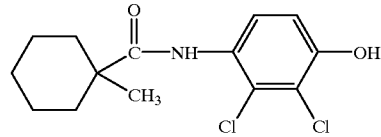

wherein the compound of group (A) is 1,1'-iminiodi (octamethylene diguanidinium tris(alkyl-benzenesulfonate) of the formula

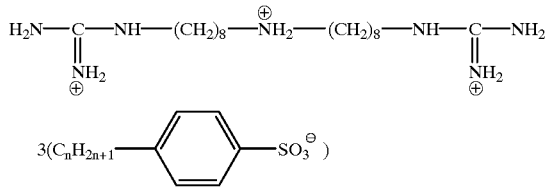

n=10 to 13.
2. Compositions according to claim 1 wherein the weight ratio of active compounds of group (A) to the active compound of the formula (II) is between 1:0.5 and 1:10.
3. Method for the control of fungi, comprising the step of applying effective active compound compositions according to claim 1 to the fungi or to their habitat or both.
4. Process for the preparation of fungicidal compositions, comprising the step of mixing active compound combinations according to claim 1 with one of the group containing extenders and surface-active agents.

* * * * *